(12) United States Patent
Yang et al.

(10) Patent No.: US 9,187,695 B2
(45) Date of Patent: Nov. 17, 2015

(54) PHOSPHORUS—SILICON SYNERGISTIC FLAME RETARDANTS AND THE PREPARATION METHOD AND USE THEREOF

(75) Inventors: Shiyong Yang, Beijing (CN); Tao Song, Beijing (CN); Jingang Liu, Beijing (CN)

(73) Assignee: Institute of Chemistry, Chinese Academy of Sciences, Beijing (CN)

( * ) Notice: Subject to any disclaimer, the term of this patent is extended or adjusted under 35 U.S.C. 154(b) by 110 days.

(21) Appl. No.: 14/116,340

(22) PCT Filed: Apr. 13, 2012

(86) PCT No.: PCT/CN2012/000514
§ 371 (c)(1),
(2), (4) Date: Nov. 7, 2013

(87) PCT Pub. No.: WO2013/134900
PCT Pub. Date: Sep. 19, 2013

(65) Prior Publication Data
US 2014/0094620 A1    Apr. 3, 2014

(30) Foreign Application Priority Data
Mar. 12, 2012 (CN) .......................... 2012 1 0063638

(51) Int. Cl.
| | |
|---|---|
| *C07F 9/02* | (2006.01) |
| *C09K 21/12* | (2006.01) |
| *C07F 9/6596* | (2006.01) |
| *C08K 5/5419* | (2006.01) |
| *C08K 5/549* | (2006.01) |
| *C07F 9/53* | (2006.01) |

(52) U.S. Cl.
CPC ............... *C09K 21/12* (2013.01); *C07F 9/5325* (2013.01); *C07F 9/5333* (2013.01); *C07F 9/6596* (2013.01); *C08K 5/549* (2013.01); *C08K 5/5419* (2013.01)

(58) Field of Classification Search
CPC ............................... C09K 21/12; C07F 9/5333
USPC ........................................................ 556/405
See application file for complete search history.

(56) References Cited

FOREIGN PATENT DOCUMENTS

| CN | 1944446 A | 4/2007 |
|---|---|---|
| CN | 101445520 A | 6/2009 |

OTHER PUBLICATIONS

Hoyt, et al., Polysiloxane networks with hydrogen bonding pendant moieties, Proceedings of the 24th Annual Meeting of the Adhesion Society (2001), pp. 474-476.*
Chojnowski, et al., Synthesis of polysiloxanes with electron-donating groups by anionic ring-opening polymerization Makromolekulare Chemie, Macromolecular Symposia (1993), 73 (Internatl Symp on Ring-Opening Polymerization, 1992), 183-201.*
Hoyt et al., Proc. of the 24th Annual Meeting of the Adhesion Soc., 2001, pp. 474-476.*
State Intellectual Property Office of China, International Search Report of PCT/CN2012/000514, Jan. 3, 2013, 6 pages.
Li, Q. et al. "Synergistic Effect of Phosphorus, Nitrogen, and Silicon on Flame-Retardant Properties and Char Yield in Polypropylene." Journal of Applied Polymer Science vol. 96, No. 3, pp. 854-860, Feb. 2005.
Wilkie, C. A. et al., "Fire Retardancy of Polymeric Materials", CRC Press, pp. 1-14, Published Dec. 10, 2009, 20 pages.
Hoyt, J. K. et al., "Polysiloxane Networks with Hydrogen Bonding Pendant Moieties", Proceedings of the 24th Annual Meeting of the Adhesion Society, Feb. 2001, 3 pages.

* cited by examiner

*Primary Examiner* — Porfirio Nazario Gonzalez
*Assistant Examiner* — Kofi Adzamli
(74) *Attorney, Agent, or Firm* — Alleman Hall McCoy Russell & Tuttle LLP

(57) ABSTRACT

The present invention discloses a phosphorus-silicon synergistic flame retardant and the preparation method and use thereof. The phosphorus-silicon synergistic flame retardant provided by the present invention has a structural general formula shown as formula I. A new type of compound containing phosphorus and silicon is prepared by the present invention using the cheap organic boron catalyst, and employing the addition reaction of diphenyl phosphine oxide and derivatives thereof with silicone containing carbon-carbon double bond. Such compounds have the properties of hydrolytic resistance, easy purification, and low synthesis cost, etc. Phosphorus and silicon elements in the molecular structures of such compounds both can act as the flame retardants solely, and meantime can work synergistically, thereby enduing the common polymeric materials with the excellent flame retardant property.

(formula I)

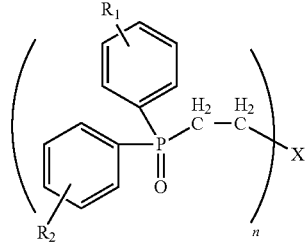

10 Claims, 10 Drawing Sheets

PHOSPHORUS—SILICON SYNERGISTIC FLAME RETARDANTS AND THE PREPARATION METHOD AND USE THEREOF

CROSS-REFERENCE TO RELATED APPLICATIONS

This is the U.S. National Phase of International PCT Application Serial No. PCT/CN2012/000514, filed Apr. 13, 2012, which claims priority to Chinese Patent Application No. 201210063638.0, filed on Mar. 12, 2012, both of which are hereby incorporated by reference in their entirety for all purposes

TECHNICAL FIELD

The present invention belongs to the flame retardant field, and relates to phosphorus-silicon synergistic flame retardants and the preparation method and use thereof.

BACKGROUND ART

In recent years, as the environmental protection and the safety protection consciousness continuously increase, the flame retardant problem of the polymeric materials gets more and more attention. It is the most effective manner to add flame retardants into polymeric bulk to improve the flame retardant property of the polymeric materials. Ideal flame retardants not only have the high-effective flame retardant feature, but also have the characteristics such as the environment friendliness, etc. At present, for the selection of the flame retardants, the following five aspects generally need to be sufficiently considered: (1) the flame retardant efficiency of the flame retardants on the polymeric materials; (2) the influence of the flame retardants on the processing technology of the polymeric materials; (3) the compatibility of the flame retardants with the matrix and the influence of the flame retardants on the physical property of the matrix; (4) the balance of the performance-price ratio of the flame retardants; and (5) the environmental compatibility of the flame retardants and the like. The conventional polymeric materials use flame retardants, such as halogen and antimony flame retardants, and although they have good flame retardant efficacy, use thereof is increasingly restricted due to their bad environmental compatibility. In contrast, the research and use of the phosphorus, nitrogen, silicon and inorganic hydrate flame retardants have been rapidly developed in recent years (Wilkie C A, Morgan A B. *Fire retardancy of polymeric materials*, CRC Press, 2010, pp 1~14).

During the research and development of the new type of flame retardants, another development trend is to pay increasing attention to the function of "synergistic effect" in a flame retardant system. In the flame retardant design of the polymeric materials, people increasingly realize that use of single flame retardant system tends to have defects, such as low efficiency, large addition amount, great influence on the property of the polymeric bulk, and the like. However, use of the synergistic effect among the different kinds of the flame retardants can largely improve the flame retardant efficiency. "Synergistic effect" means that, when the addition amounts are the same, the performance improvement of the system consisting of two or more components is superior to the sum of performance improvements when two components solely work respectively. For the flame retardants, the "halogen-antimony" and "phosphorus-nitrogen" flame retardant systems are the two most common synergistic systems. Because of the implementation of European Environmental Law, mainly WEEE and ROHS ACTs, the use of the "halogen-antimony" synergistic system is gradually forbidden. Therefore, the current synergistic flame retardant system is mainly the "phosphorus-nitrogen" system. For example, FUSHIMI Pharmaceutical Co., Ltd., Japan, develops the highly-efficient "phosphorus-nitrogen" synergistic flame retardant polyphosphazene (trade name: Rabitle® FP-100). This flame retardant has excellent flame retardant characteristic to epoxy molding compound and engineering plastic (polycarbonate, ABS resin, high impact polystyrene etc.) system.

In recent years, another kind of synergistic flame retardant system, "phosphorus-silicon" flame retardants, gets more attention. Research indicates that the coexistence of phosphorus and silicon elements has the effect of synergistic flame retardance. Research by Li et al. has found that the phosphorus-nitrogen-silicon type flame retardants have a good synergistic flame retardant effect on polypropylene materials (Li Q, et al. *Synergistic effect of phosphorus, nitrogen, and silicon on flame-retardant properties and char yield in polypropylene*. J. Appl. Polym. Sci., 2005, 96: 854-860). Patent ZL 200710178086.7 reports an organosilicon compound containing phosphorus. This compound is prepared by reacting 9,10-dihydro-9-oxa-10-phosphaphenanthrene-10-oxide (DOPO) with silicone compounds containing carbon-carbon double bonds under the action of a catalyst such as platinic chloride, rhodium chloride and the like. The research indicates that such compounds all have good flame retardant effects on the polymeric materials such as phenolic resin, polycarbonate, polymethyl methacrylate, etc. However, there is an easily hydrolyzable phosphonate ester bond in the molecular structure of such compounds, thus their use is limited. In addition, because the preparation reaction uses the expensive heavy metal catalyst, the cost is high, and it is difficult to achieve the mass production.

CONTENTS OF THE INVENTION

The present invention aims to provide a phosphorus-silicon synergistic flame retardant and the preparation method and use thereof.

The present invention provides phosphorus-silicon synergistic flame retardants, namely the compounds represented by formula I,

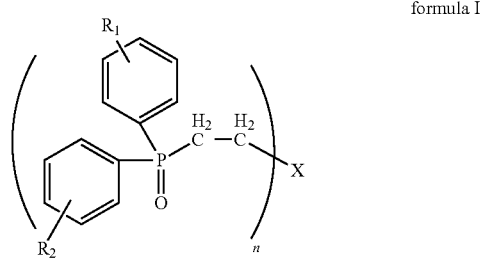

formula I in formula I, the repeating structural units are connected with X group, both $R_1$ and $R_2$ are selected from the group consisting of any one of H and alkyl that has total carbon atoms of 1-4; n is an integer of 1-20, particularly an integer of 2-8, more particularly an integer of 2-4, 2-6, 4-8 or 6-8 or 4-6; X is

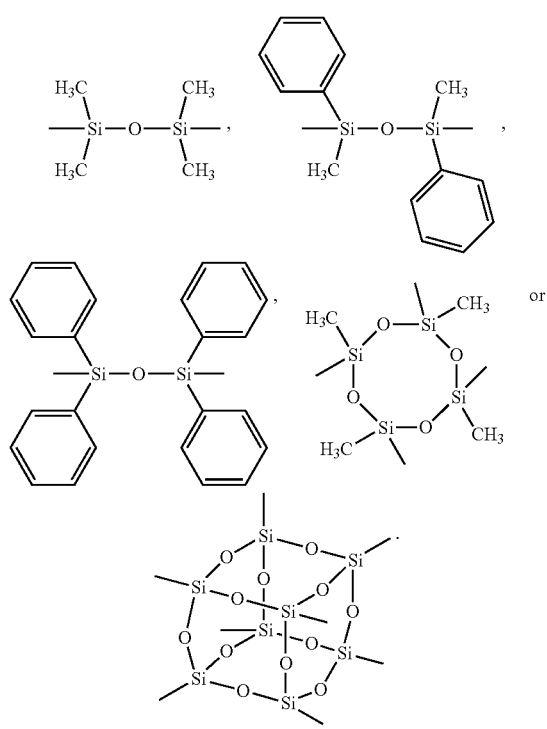

The present invention provides the method for preparing the compounds represented by formula I, comprising the following steps: after dissolving the compounds represented by formula II and vinylsiloxanes represented by formula III in solvent a, adding an organic boron solution into this system for reaction, and then obtaining the compounds represented by formula I after the completion of the reaction;

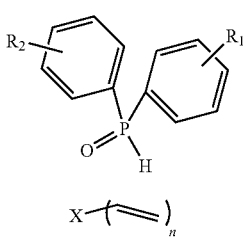

formula II formula III in formula II and formula III, the definitions of $R_1$, $R_2$, n, and X are all the same as the previous definitions.

The reaction equation of the above method is shown as follows:

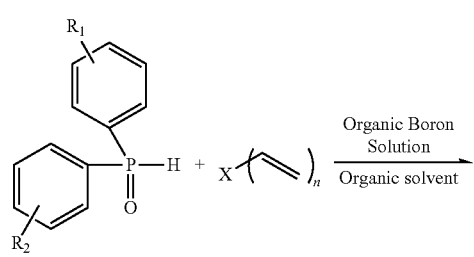

In the above method, the solvent a is selected from the group consisting of at least one of alcohol compounds, saturated hydrocarbon compounds, aromatic compounds, nitrile compounds, ketone compounds, tetrahydrofuran, 1,4-dioxane, N,N-dimethylformamide, N,N-dimethylacetamide, dimethylsulfoxide and N-methyl-2-pyrrolidone; wherein, the alcohol compounds are selected from the group consisting of at least one of methanol, ethanol, propanol, pentanol, n-butanol, isopropanol, isobutanol, isopentanol, glycol and ethylene glycol monomethyl ether, particularly at least one of methanol, ethanol, propanol and isopropanol; wherein the saturated hydrocarbon compounds are selected from the group consisting of at least one of pentane, hexane, heptane, octane, nonane, decane, cyclopentane, cyclohexane and cycloheptane, particularly at least one of pentane, hexane, heptane, cyclopentane and cyclohexane; the aromatic compounds are selected from the group consisting of at least one of benzene, toluene and xylene, particularly at least one of toluene and xylene; the nitrile compounds are selected from the group consisting of at least one of acetonitrile and propionitrile, particularly acetonitrile; the ketone compounds are selected from the group consisting of at least one of acetone, butanone, 2-butanone and 2-pentanone, particularly at least one of acetone, butanone and 2-butanone;

Said organic boron is selected from the group consisting of at least one of trimethyl boron, triethyl boron, tripropyl boron, triisopropyl boron, tributyl boron and triphenyl boron; in the organic boron solution, the solvent is selected from the group consisting of at least one of ethyl ether, tetrahydrofuran and n-hexane.

The feeding molar ratio of the compounds represented by formula II and vinylsiloxanes represented by formula III is n:1, wherein, n is an integer of 1-20, particularly an integer of 2-8, more particularly an integer of 2-4, 2-6, 4-8 or 6-8 or 4-6;

The usage ratio of the solvent a and the compounds represented by formula II is 100~2000 ml:1 mol, particularly 500~1500 ml:1 mol, more particularly 450-1500:1, 750-1000:1, 825-1000:1, 450-1000:1, 450-750:1, 450-825:1, 825-1500:1, 750-825:1, 750-1500:1, 825-1500:1, or 1000-1500:1.

In the dissolving step, the temperature is 0~50° C., particularly 10~45° C., more particularly 0-35° C., 5-27° C., 5-45° C., 0-45° C., 20-45° C., 25-45° C., 35-45° C., 20-25° C., 20-35° C., or 5-25° C.

The concentration of the organic boron solution is 0.1M~10M, particularly 0.5~5M, more particularly 0.1-5M, 0.2-3M, 0.5-2M, 1-5M, 0.1-3M, 0.1-2M, 0.1-0.5M, 0.2-5M, 0.2-3M, 0.2-2M, or 0.5-5M; the feeding molar ratio of the organic boron and the compounds represented by formula II is 0.01~10:1, particularly 0.1~5:1, more particularly 0.1-6:1, 0.12-5:1, 0.2-0.75:1, 0.45-6:1, 0.45-5:1, 0.2-6:1, 0.2-5:1, 0.2-1:1, 0.45-0.75:1, 0.75-6:1, 0.75-5:1, 1-6:1, 1-5:1, or 5-6:1.

In the reacting step, the temperature is 0-50° C., particularly 10~45° C., more particularly 0-45° C., 5-35° C., 10-27° C., 20-25° C., 0-35° C., 10-35° C., 0-27° C., 10-27° C., or 10-27° C., the time is 0.5~40 hours, particularly 1~35 hours, more particularly 1.5-38 hours, 1.5-35 hours, 2-35 hours, 12-32 hours, 14-24 hours, or 22-38 hours; because the reaction catalyzed by the organic boron is comparatively violent, in the actual operation, the dropwise addition manner can be used to blend the organic boron solution and the reaction system, this reaction step particularly is: firstly dropwise adding the organic boron solution into the reaction system, then continuing the reaction for a period of time after the completion of the dropwise addition; wherein, the time of the dropwise addition can be 0.5~20 hours, particularly 1~16 hours, more particularly 0.5-12 hours, 0.5-10 hours, 0.5-6 hours, 1-6 hours, 1-20 hours, 1-12 hours, 1-10 hours, 1-6 hours, 6-20 hours, 6-12 hours, or 12-20 hours; the time continuing the reaction after the completion of the dropwise addition is 1-25 hours, particularly 1~18 hours, more particularly 4-18 hours, 4-16 hours, 4-12 hours, 4-6 hours, 1-18 hours, 1-16 hours, 1-12 hours, 1-6 hours, or 4-25 hours; both the adding step and reacting step are preformed in the inert atmosphere; the inert atmosphere is selected from the group consisting of at least one of nitrogen atmosphere and argon atmosphere, particularly nitrogen atmosphere.

In addition, the flame retardant materials of the compounds represented by formula I provided by the above present invention and use of the compounds represented by formula I for preparing flame retardant materials belong to the protection scope of the present invention, wherein the flame retardant materials are selected from the group consisting of at least one of flame retardant thermoplastic engineering plastic, flame retardant thermosetting resin composition, flame retardant encapsulating materials, flame retardant adhesive, flame retardant laminated ply and flame retardant fiber reinforced materials, the flame retardant encapsulating materials particularly are flame retardant integrated circuit encapsulating materials.

MODE OF CARRYING OUT THE INVENTION

Figure 1:
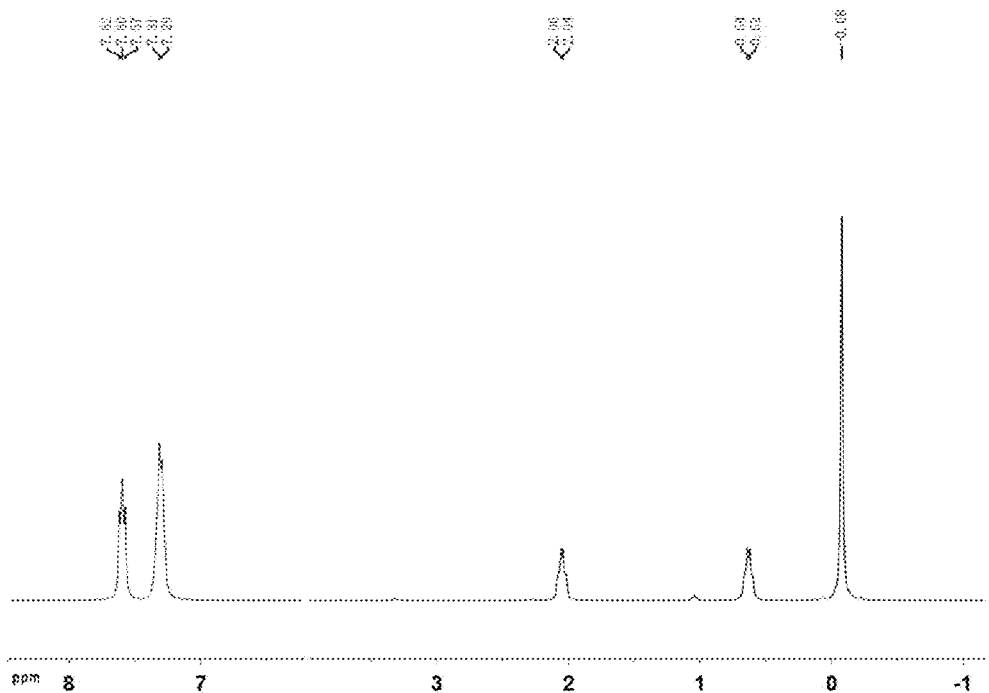
FIG. 1 is the nuclear magnetic hydrogen spectrogram of the compound 1 prepared by Example 1.

The following examples illustrate the present invention in combination with the particular examples, however, the present invention is not limited to the following examples. The methods as described are all the conventional methods, unless specifically specified. Said raw materials all can be available from the public commercial approach, unless specifically specified.

The properties of the prepared epoxy resin compositions are all tested according to the following method in the following examples (the test methods are all the conventional methods, unless specifically specified):

1) flame retardance test (ASTM UL94 or GB/T 2408-2008 standard): CZF-3 type Horizontal-vertical combustion tester.
2) the tests to the stretching and bending performances of the plastic and composite are tested on (GB/T 1040.1-2006 and GB/T9341-2000) Instron 3365 universal testing machine, the drawing and extruding speeds are 2.0 mm/min. Test temperature: normal temperature.

EXAMPLE 1

In a reactor equipped with nitrogen inlet, condensation tube and thermometer, 4.04 g (0.02 mol) of diphenyl phosphine oxide (DPPO) and 1.86 g (0.01 mol) of 1,1,3,3-tetramethyl-1,3-divinyldisiloxane were sequentially added into 10 ml of acetone, and stirred to be clear and transparent at 10° C., then 4 ml 0.5M of solution of tributyl boron in tetrahydrofuran was dropwise added in 0.5 hours at the maintained temperature of 10° C. under nitrogen protection; after the completion of dropwise addition, the reaction was kept at 10° C. for 1 hour before it was stopped, evaporating the solvent, washing with water several times, and drying, thereby obtaining 5.25 g of the white solid (compound 1), yield 89%.

Figure 2:
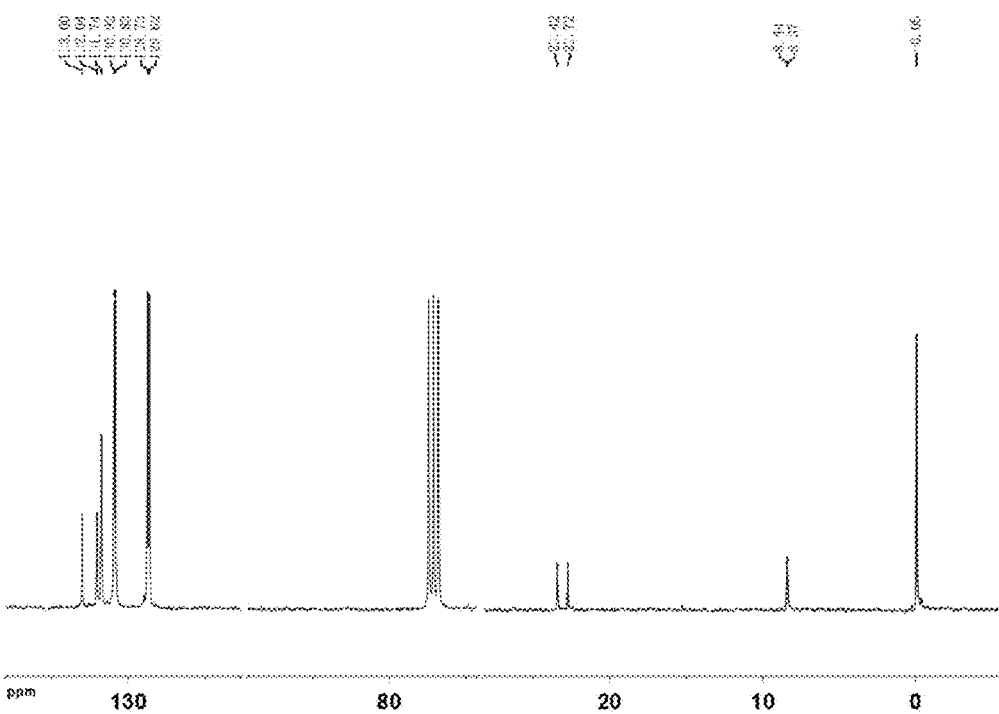
FIG. 2 is the nuclear magnetic carbon spectrogram of the compound 1 prepared by Example 1.
Figure 3:
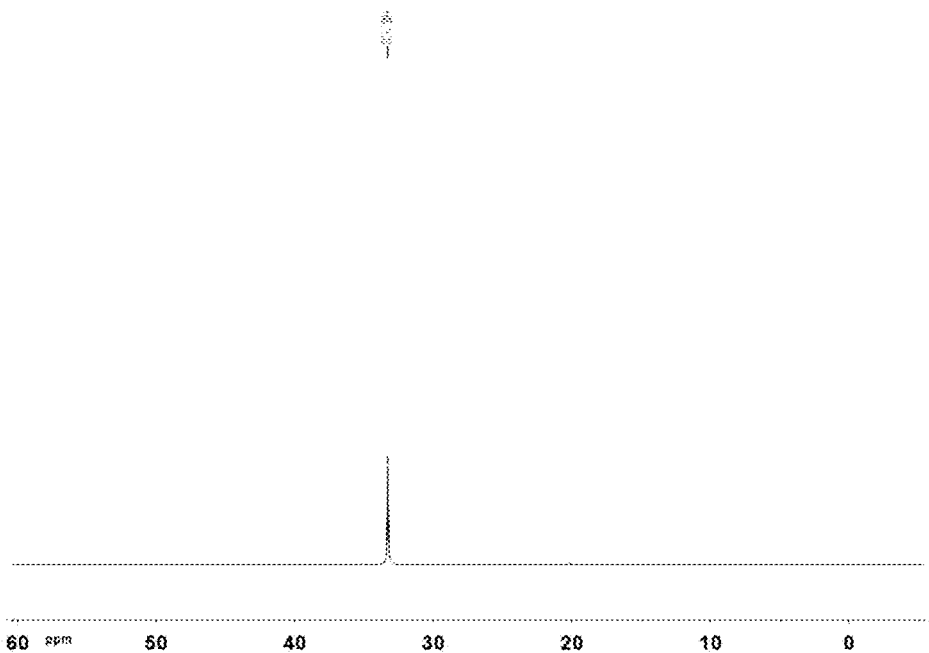
FIG. 3 is the nuclear magnetic phosphorus spectrogram of the compound 1 prepared by Example 1.
Figure 4:
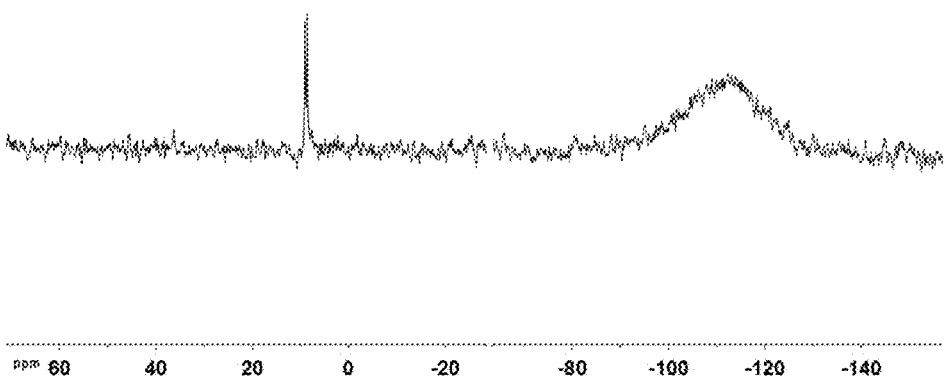
FIG. 4 is the nuclear magnetic silicon spectrogram of the compound 1 prepared by Example 1.
Figure 5:
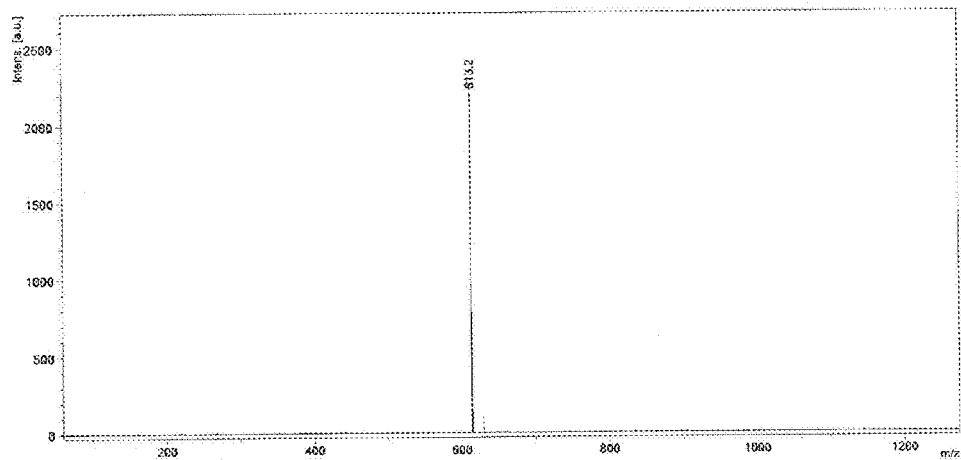
FIG. 5 is the mass spectrogram (MALDI-TOF) of the compound 1 prepared by Example 1.
Figure 6:
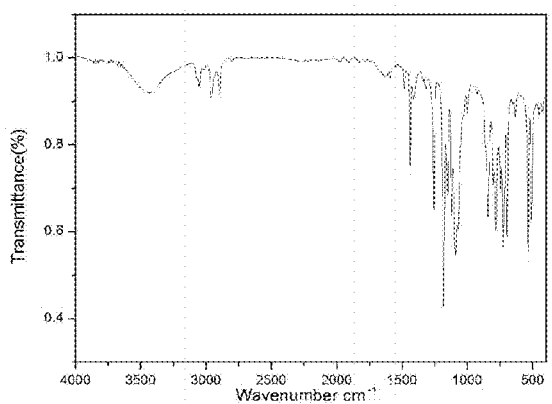
FIG. 6 is the infrared spectrogram of the compound 1 prepared by Example 1.
Figure 7:
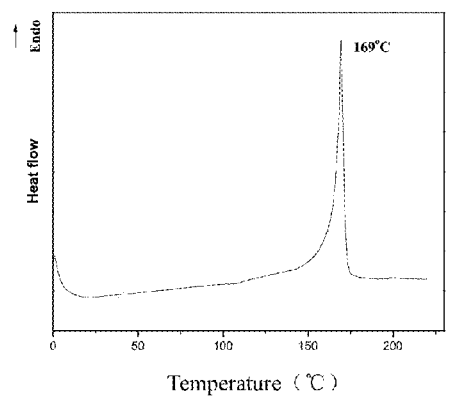
FIG. 7 is the differential scanning calorimetric (DSC) drawing of the compound 1 prepared by Example 1.

The structural test datum of this compound are shown as follows (nuclear magnetic hydrogen spectrogram, nuclear magnetic carbon spectrogram, nuclear magnetic phosphorus spectrogram, nuclear magnetic silicon spectrogram, mass spectrogram (MALDI-TOF),infrared spectrogram and DSC spectrogram of this compound are shown in FIG. 1, FIG. 2, FIG. 3, FIG. 4, FIG. 5, FIG. 6 and FIG. 7, respectively):

melting point: 169° C. (DSC peak temperature).

nuclear magnetic hydrogen spectrum ($CDCl_3$, 400 Hz, ppm): −0.08 (s, 12H), 0.63 (d, 4H), 2.05 (d, 4H), 7.30 (d, 6H), 7.60 (t, 4H).

nuclear magnetic carbon spectrum ($CDCl_3$, 400 Hz, ppm): −0.05, 8.43, 23.4, 77.1, 128.7, 130.9, 131.7, 133.0.

nuclear magnetic phosphorus spectrum ($CDCl_3$, 300 Hz, ppm): 33.28.

nuclear magnetic silicon spectrum (CDCl₃, 300 Hz, ppm): 8.63.

mass spectrum (MALDI-TOF): 613.2, (M⁺+Na⁺).

elementary analysis (%): theoretical value, C, 65.06; H, 6.82, measured value, C, 64.70; H, 6.85.

infrared spectrum (cm⁻¹): 3052, 2958, 2899, 1483, 1437, 1410, 1318, 1255, 1183, 1150, 1120, 1091, 999, 842.

It can be seen from the above, the structure of this product is correct, and is the compound represented by formula I. Its structural formula is shown as follows:

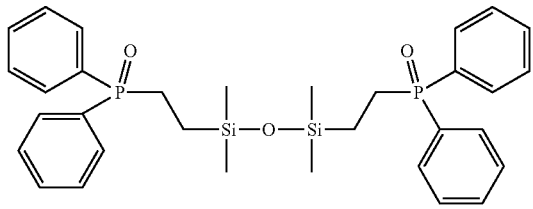

EXAMPLE 2

In a reactor equipped with nitrogen inlet, condensation tube and thermometer, 40.4 g (0.2 mol) of diphenyl phosphine oxide (DPPO) and 18.6 g (0.1 mol) of 1,1,3,3-tetramethyl-1,3-divinyldisiloxane were sequentially added into 300 ml of tetrahydrofuran, and stirred to be clear and transparent at 45° C., then 200 ml 5M of solution of tripropyl boron in ethyl ether was dropwise added in 20 hours at the maintained temperature of 45° C. under nitrogen protection; after the completion of dropwise addition, the reaction was kept at 45° C. for 18 hours before it was stopped, evaporating the solvent, washing with water several times, and drying, thereby obtaining 50.2 g of the white solid (compound 1), yield 85%.

The structural test datum of this compound are shown as follows (nuclear magnetic hydrogen spectrogram, nuclear magnetic carbon spectrogram, nuclear magnetic phosphorus spectrogram, nuclear magnetic silicon spectrogram, mass spectrogram (MALDI-TOF), infrared spectrogram and DSC spectrogram of this compound were the same as those in Example 1):

melting point: 169° C. (DSC peak temperature).

nuclear magnetic hydrogen spectrum (CDCl₃, 400 Hz, ppm): −0.08 (s, 12H), 0.63 (d, 4H), 2.05 (d, 4H), 7.30 (d, 6H), 7.60 (t, 4H).

nuclear magnetic carbon spectrum (CDCl₃, 400 Hz, ppm): −0.05, 8.43, 23.4, 77.1, 128.7, 130.9, 131.7, 133.0.

nuclear magnetic phosphorus spectrum (CDCl₃, 300 Hz, ppm): 33.28.

nuclear magnetic silicon spectrum (CDCl₃, 300 Hz, ppm): 8.63.

mass spectrum (MALDI-TOF): 613.2, (M⁺+Na⁺).

elementary analysis (%): theoretical value, C, 65.06; H, 6.82; measured value, C, 64.70; H, 6.85.

infrared spectrum (cm⁻¹): 3052, 2958, 2899, 1483, 1437, 1410, 1318, 1255, 1183, 1150, 1120, 1091, 999, 842.

The structural formula is shown as in Example 1.

EXAMPLE 3

In a reactor equipped with nitrogen inlet, condensation tube and thermometer, 4.04 g (0.02 mol) of diphenyl phosphine oxide (DPPO) and 3.1 g (0.01 mol) of 1,3-dimethyl-1,3-diphenyl-1,3-divinyldisiloxane were sequentially added into 20 ml of methanol, and stirred to be clear and transparent at 5° C., then 15 ml 1M of solution of tributyl boron in ethyl ether was dropwise added in 20 hours at the maintained temperature of 5° C. under nitrogen protection; after the completion of dropwise addition, the reaction was kept at 5° C. for 12 hours before it was stopped, evaporating the solvent, washing with water several times, and drying, thereby obtaining 6.43 g of the white solid (compound 2), yield 90%.

mass spectrum (MALDI-TOF): 714.2, (M⁺+Na⁺).

elementary analysis (%): theoretical value, C, 65.06; H, 6.82; measured value, C, 64.70; H, 6.85.

infrared spectrum (cm⁻¹): 3051, 2955, 2894, 1480, 1434, 1412, 1319, 1250, 1182, 1147, 1121, 1091, 999.

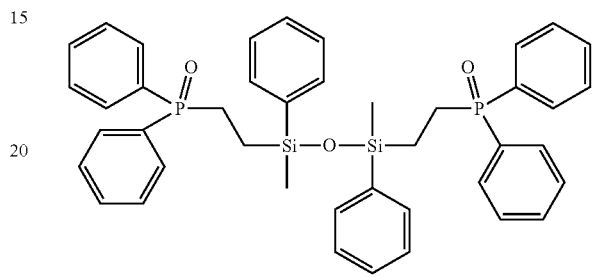

EXAMPLE 4

In a reactor equipped with nitrogen inlet, condensation tube and thermometer, 40.4 g (0.2 mol) of diphenyl phosphine oxide (DPPO) and 43.4 g (0.1 mol) of 1,1,3,3-tetraphenyl-1,3-divinyldisiloxane were sequentially added into 300 ml of ethylene glycol monomethyl ether, and stirred to be clear and transparent at 25° C., 400 ml 3M of solution of triisopropyl boron in tetrahydrofuran was dropwise added in 10 hours at the maintained temperature of 25° C. under nitrogen protection; after the completion of dropwise addition, the reaction was kept at 25° C. for 25 hours before it was stopped, evaporating the solvent, washing with water several times, and drying, thereby obtaining 69.6 g of the white solid (compound 3), yield 83%.

mass spectrum (MALDI-TOF): 861.3, (M⁺+Na⁺).

elementary analysis (%): theoretical value, C, 74.44; H, 5.77; measured value, C, 74.78; H, 5.72.

infrared spectrum (cm⁻¹): 3052, 1484, 1435, 1408, 1317, 1255, 1182, 1148, 1121, 1093, 996.

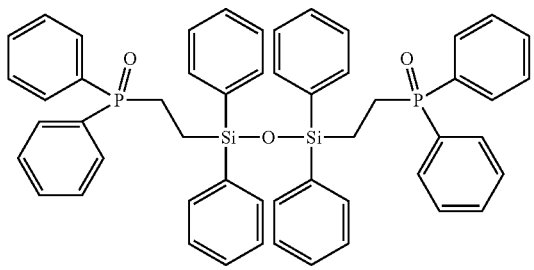 [SMILES: O=P(CC[Si](O[Si](CCP(=O)(c1ccccc1)c1ccccc1)(c1ccccc1)c1ccccc1)(c1ccccc1)c1ccccc1)(c1ccccc1)c1ccccc1]

EXAMPLE 5

In a reactor equipped with nitrogen inlet, condensation tube and thermometer, 8.08 g (0.04 mol) of diphenyl phosphine oxide (DPPO) and 3.45 g (0.01 mol) of tetramethyl-tetravinyl-cyclotetrasiloxane were sequentially added into 30 ml of cyclohexane, and stirred to be clear and transparent at 20° C., then 40 ml 1M of solution of triethyl boron in tetrahydrofuran was dropwise added in 1 hour at the maintained temperature of 20° C. under nitrogen protection; after the completion of dropwise addition, the reaction was kept at 20° C. for 1 hour before it was stopped, evaporating the solvent, washing with water several times, and drying, thereby obtaining 10.38 g of the white solid (compound 4), yield 89%.

Figure 8:
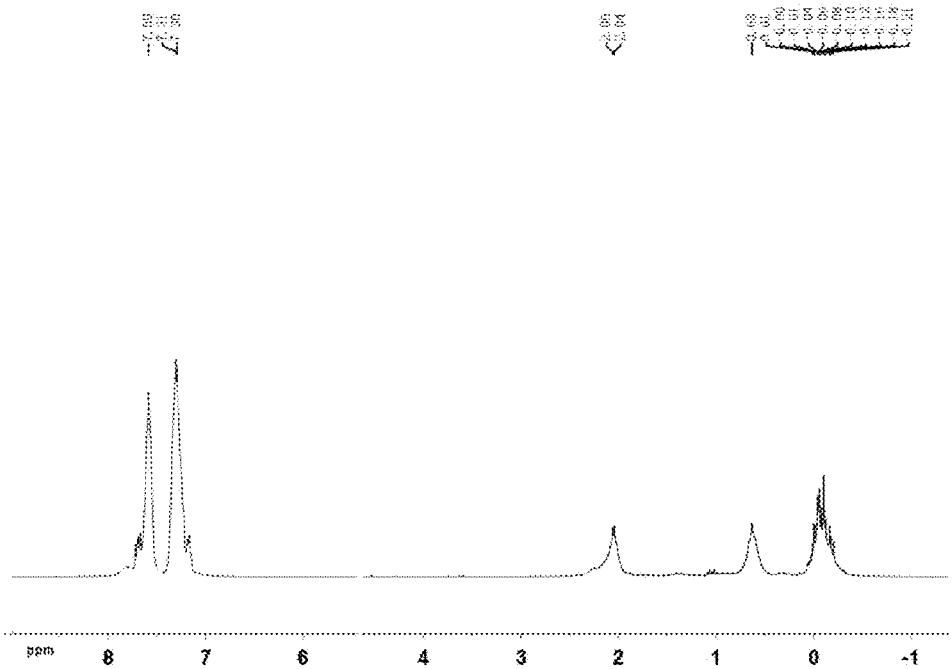
FIG. 8 is the nuclear magnetic hydrogen spectrogram of the compound 4 prepared by Example 5.
Figure 9:
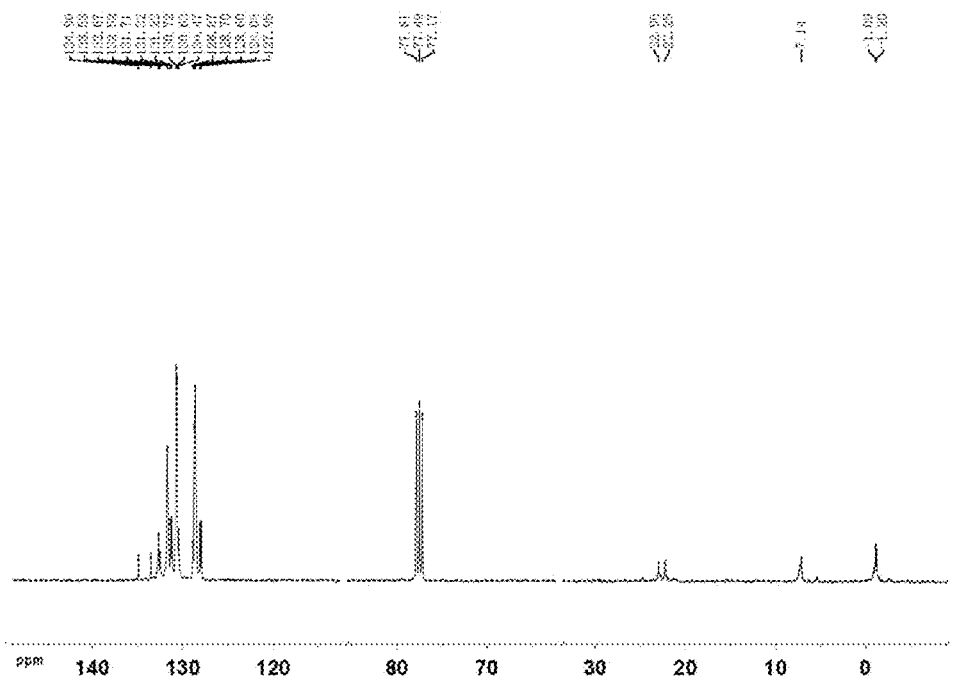
FIG. 9 is the nuclear magnetic carbon spectrogram of the compound 4 prepared by Example 5.
Figure 10:
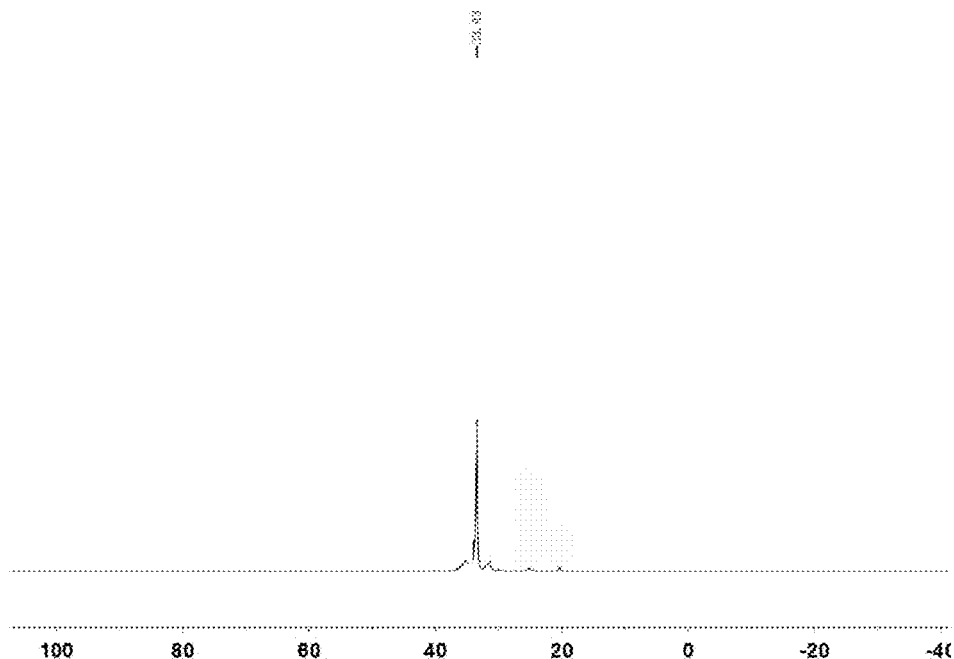
FIG. 10 is the nuclear magnetic phosphorus spectrogram of the compound 4 prepared by Example 5.
Figure 11:
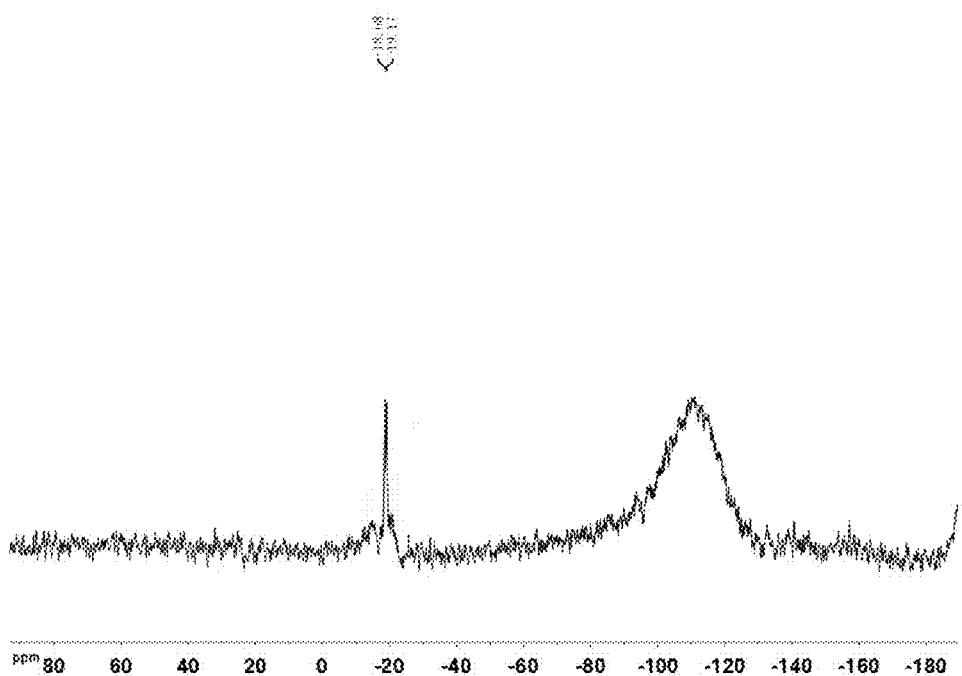
FIG. 11 is the nuclear magnetic silicon spectrogram of the compound 4 prepared by Example 5.
Figure 12:
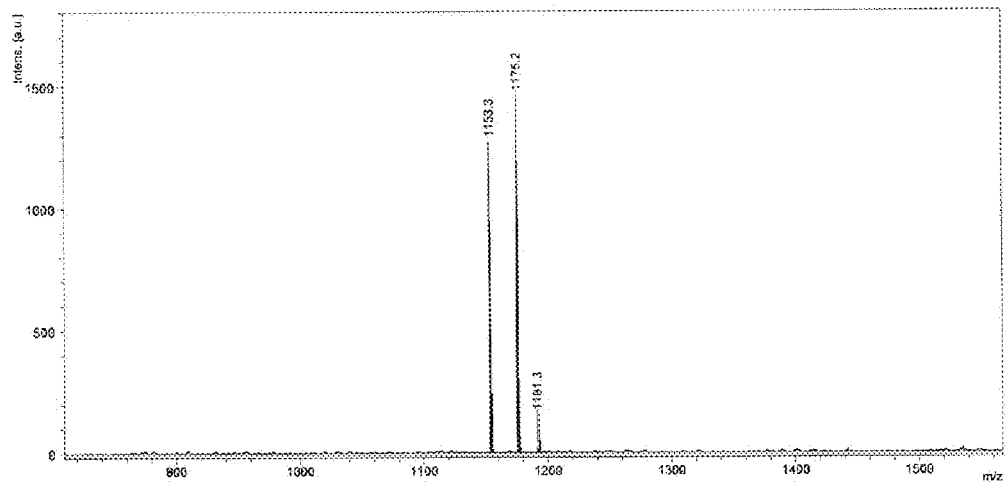
FIG. 12 is the mass spectrogram (MALDI-TOF) of the compound 4 prepared by Example 5.
Figure 13:
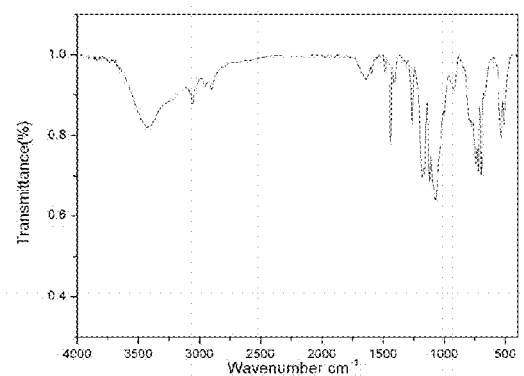
FIG. 13 is the infrared spectrogram of the compound 4 prepared by Example 5.
Figure 14:
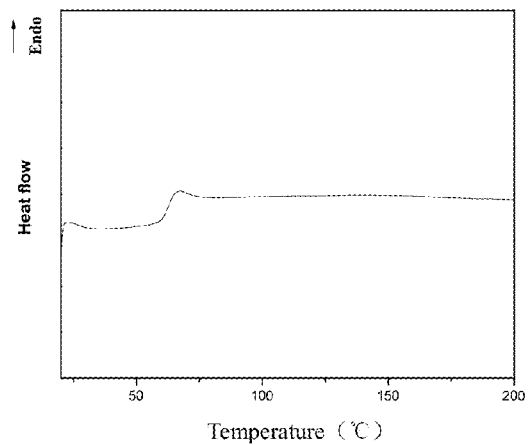
FIG. 14 is the differential scanning calorimetric (DSC) drawing of the compound 4 prepared by Example 5.

The structural test datum of this compound are shown as follows (nuclear magnetic hydrogen spectrogram, nuclear magnetic carbon spectrogram, nuclear magnetic phosphorus spectrogram, nuclear magnetic silicon spectrogram, mass spectrogram (MALDI-TOF), infrared spectrogram and DSC spectrogram of this compound are shown in FIG. 8, FIG. 9, FIG. 10, FIG. 11, FIG. 12, FIG. 13 and FIG. 14, respectively):

glass transition temperature ($T_g$, DSC): 64° C.

nuclear magnetic hydrogen spectrum (CDCl$_3$, 400 Hz, ppm): −0.06 (s, 12H), 0.59 (d, 8H), 2.01 (d, 8H), 7.22 (m, 24H), 7.61 (m, 16H).

nuclear magnetic carbon spectrum (CDCl$_3$, 400 Hz, ppm): −1.09, 7.14, 22.25, 22.96, 128.08, 128.70, 130.72, 131.22, 131.32, 131.71, 132.52, 132.67, 133.53, 134.90.

nuclear magnetic phosphorus spectrum (CDCl$_3$, 300 Hz, ppm): 33.77.

nuclear magnetic silicon spectrum (CDCl$_3$, 300 Hz, ppm): −18.69.

mass spectrum (MALDI-TOF): 1175, (M$^+$+Na$^+$).

elementary analysis (%): theoretical value, C, 62.48; H, 5.94; measured value, C, 62.70; H, 6.05.

infrared spectrum (cm$^{-1}$): 3424, 3056, 2959, 2901, 1637, 1591, 1484, 1437, 1408, 1262, 1180, 1160, 1121, 1071, 918.

It can be seen from the above, the structure of this product is correct, and is the compound represented by formula I. Its structural formula is shown as follows:

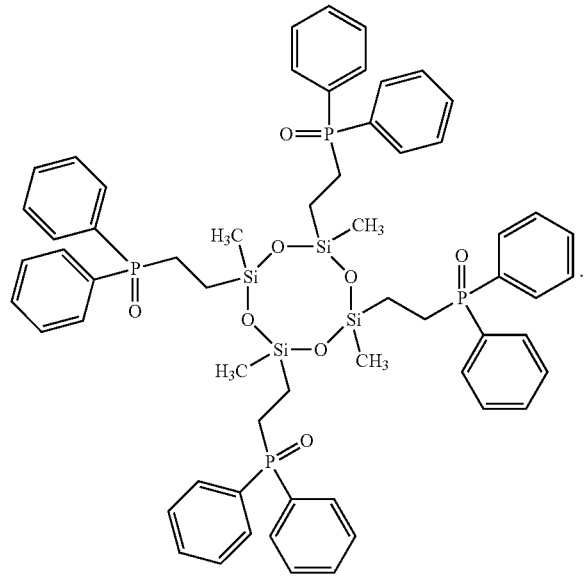 [SMILES: C[Si]1(CCP(=O)(c2ccccc2)c2ccccc2)O[Si](C)(CCP(=O)(c2ccccc2)c2ccccc2)O[Si](C)(CCP(=O)(c2ccccc2)c2ccccc2)O[Si](C)(CCP(=O)(c2ccccc2)c2ccccc2)O1]

EXAMPLE 6

In a reactor equipped with nitrogen inlet, condensation tube and thermometer, 16.16 g (0.08 mol) of diphenyl phosphine oxide (DPPO) and 6.9 g (0.02 mol) of tetramethyl-tetravinyl-cyclotetrasiloxane were sequentially added into 70 ml of acetone, and stirred to be clear and transparent at 0° C., then 4 ml 2M of solution of tributyl boron in tetrahydrofuran was dropwise added in 10 hours at the maintained temperature of 0° C. under nitrogen protection; after the completion of dropwise addition, the reaction was kept at 0° C. for 4 hours before it was stopped, evaporating the solvent, washing with water several times, and drying, thereby obtaining 20.96 g of the white solid (compound 4), yield 90%.

The structural test datum of this compound are shown as follows (nuclear magnetic hydrogen spectrogram, nuclear magnetic carbon spectrogram, nuclear magnetic phosphorus spectrogram, nuclear magnetic silicon spectrogram, mass spectrogram (MALDI-TOF), infrared spectrogram and DSC spectrogram of this compound are the same as those in Example 5, respectively):

glass transition temperature ($T_g$, DSC): 64° C.

nuclear magnetic hydrogen spectrum (CDCl$_3$, 400 Hz, ppm): −0.06 (s, 12H), 0.59 (d, 8H), 2.01 (d, 8H), 7.22 (m, 24H), 7.61 (m, 16H).

nuclear magnetic carbon spectrum (CDCl$_3$, 400 Hz, ppm): −1.09, 7.14, 22.25, 22.96, 128.08, 128.70, 130.72, 131.22, 131.32, 131.71, 132.52, 132.67, 133.53, 134.90.

nuclear magnetic phosphorus spectrum (CDCl$_3$, 300 Hz, ppm): 33.77.

nuclear magnetic silicon spectrum (CDCl$_3$, 300 Hz, ppm): −18.69.

mass spectrum (MALDI-TOF): 1175 (M$^+$+Na$^+$).

elementary analysis (%): theoretical value, C, 62.48; H, 5.94; measured value, C, 62.70; H, 6.05 infrared spectrum (cm$^{-1}$): 3424, 3056, 2959, 2901, 1637, 1591, 1484, 1437, 1408, 1262, 1180, 1160, 1121, 1071, 918.

Its structural formula is shown as in Example 5.

EXAMPLE 7

In a reactor equipped with nitrogen inlet, condensation tube and thermometer, 16.16 g (0.08 mol) of diphenyl phosphine oxide (DPPO) and 6.31 g (0.01 mol) of octavinyl cyclooctasilsesquioxane were sequentially added into 60 ml 1,4-dioxane, and stirred to be clear and transparent at 35° C., 160 ml 0.1M of solution of triethyl boron in ethyl ether was dropwise added in 12 hours at the maintained temperature of 35° C. under nitrogen protection; after the completion of dropwise addition, the reaction was kept at 35° C. for 12 hours before it was stopped, evaporating the solvent, washing with water several times, and drying, thereby obtaining 20.46 g of the white solid (compound 5), yield 91%.

Figure 15:
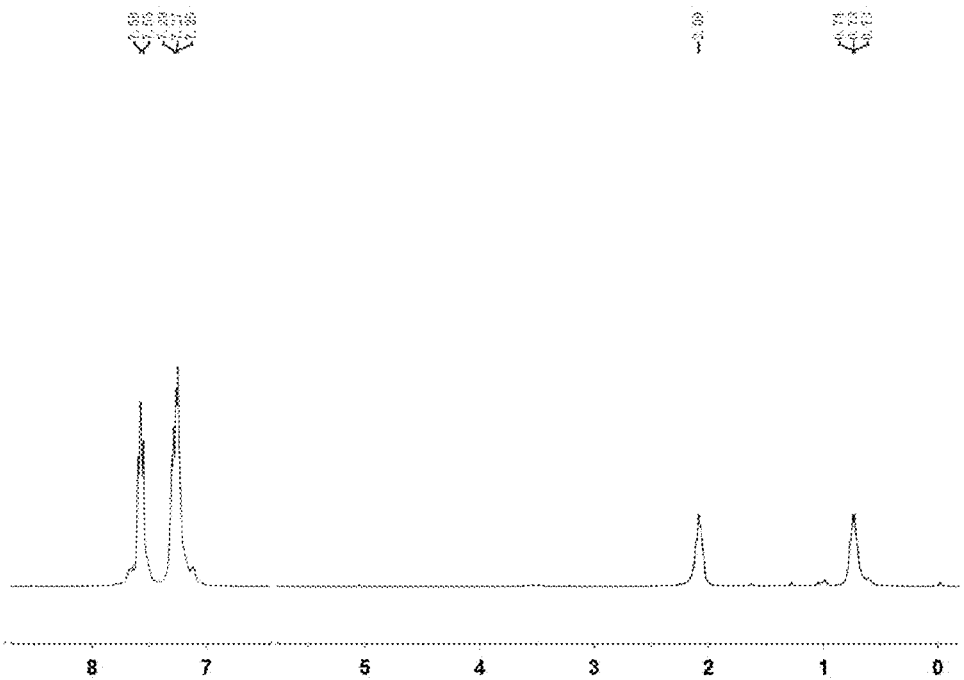
FIG. 15 is the nuclear magnetic hydrogen spectrogram of the compound 5 prepared by Example 7.
Figure 16:
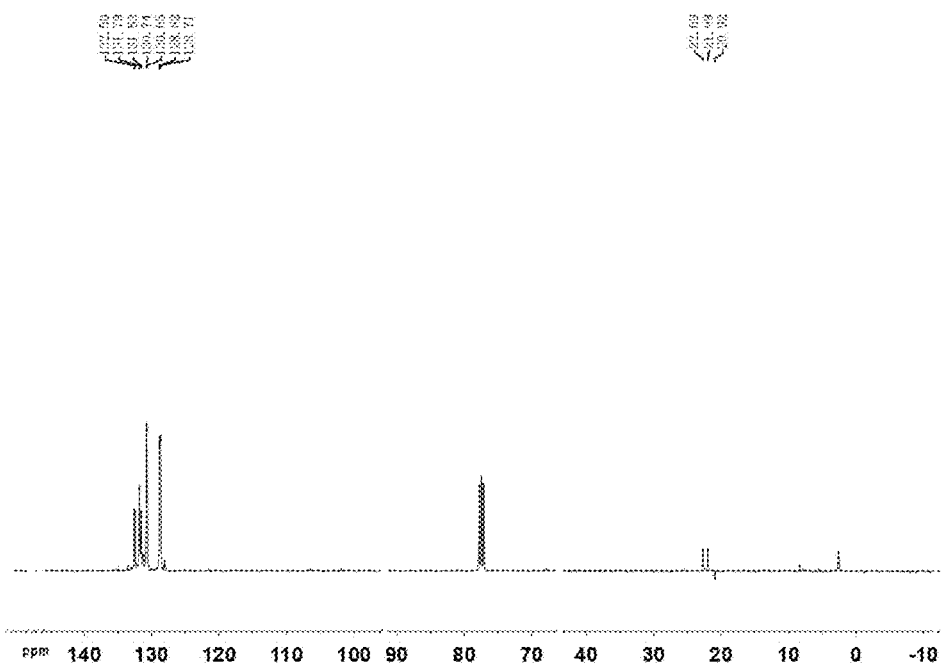
FIG. 16 is the nuclear magnetic carbon spectrogram of the compound 5 prepared by Example 7.
Figure 17:
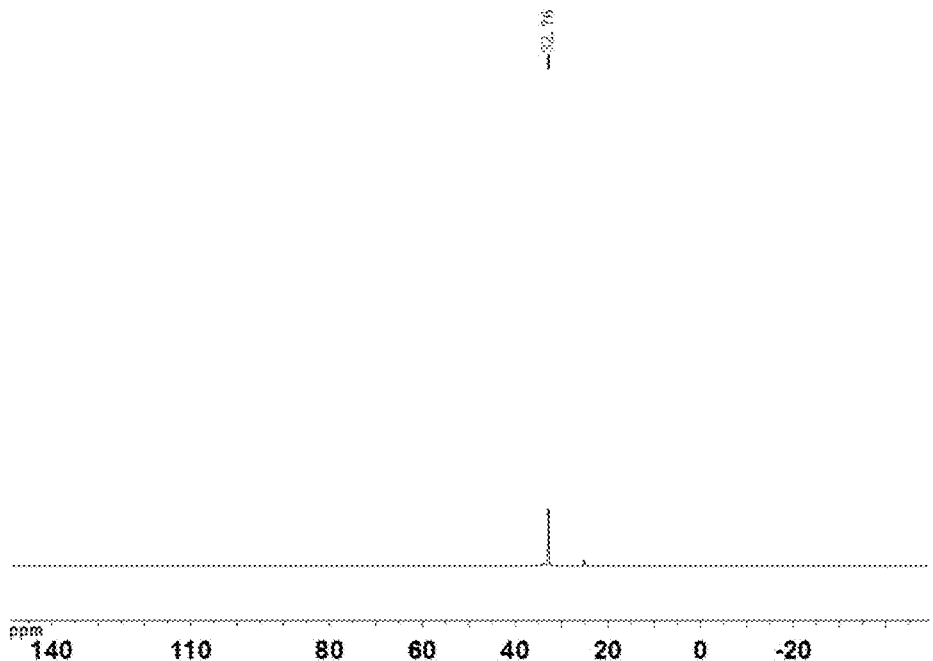
FIG. 17 is the nuclear magnetic phosphorus spectrogram of the compound 5 prepared by Example 7.
Figure 18:
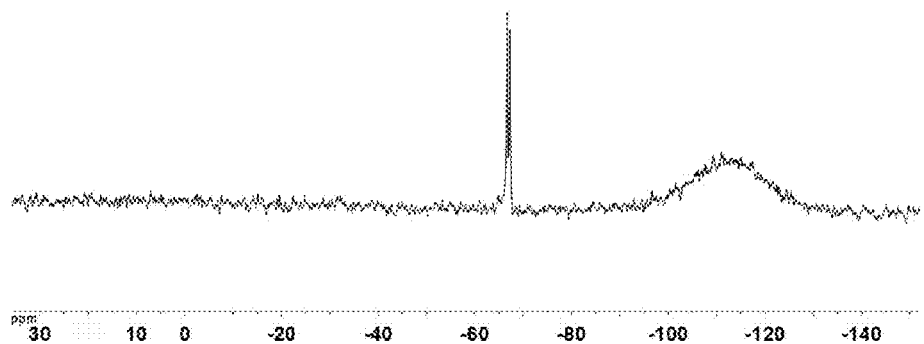
FIG. 18 is the nuclear magnetic silicon spectrogram of the compound 5 prepared by Example 7.
Figure 19:
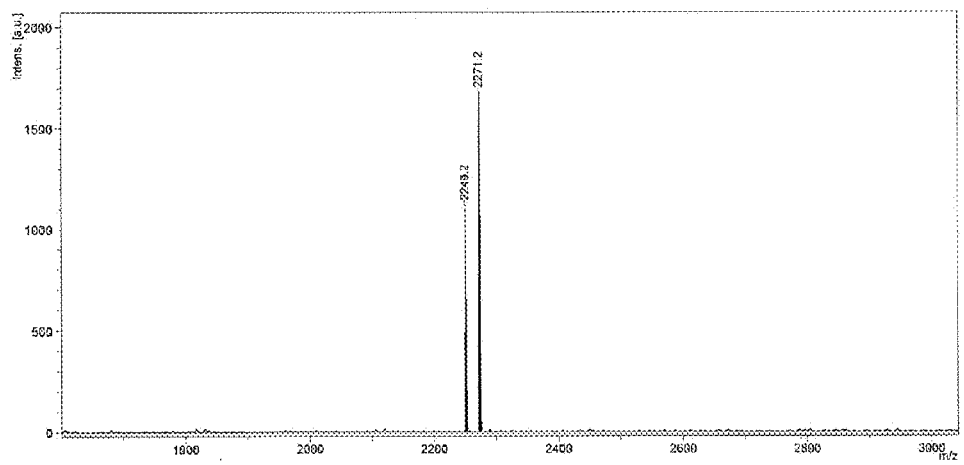
FIG. 19 is the mass spectrogram (MALDI-TOF) of the compound 5 prepared by Example 7.
Figure 20:
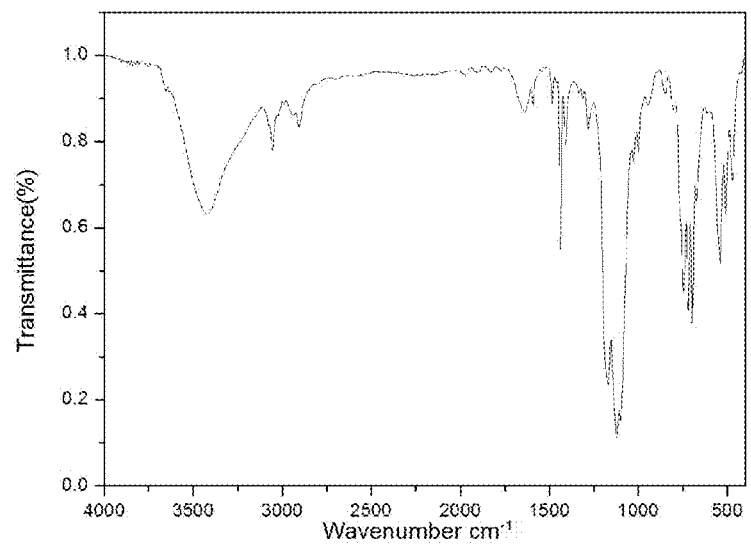
FIG. 20 is the infrared spectrogram of the compound 5 prepared by Example 7.
Figure 21:
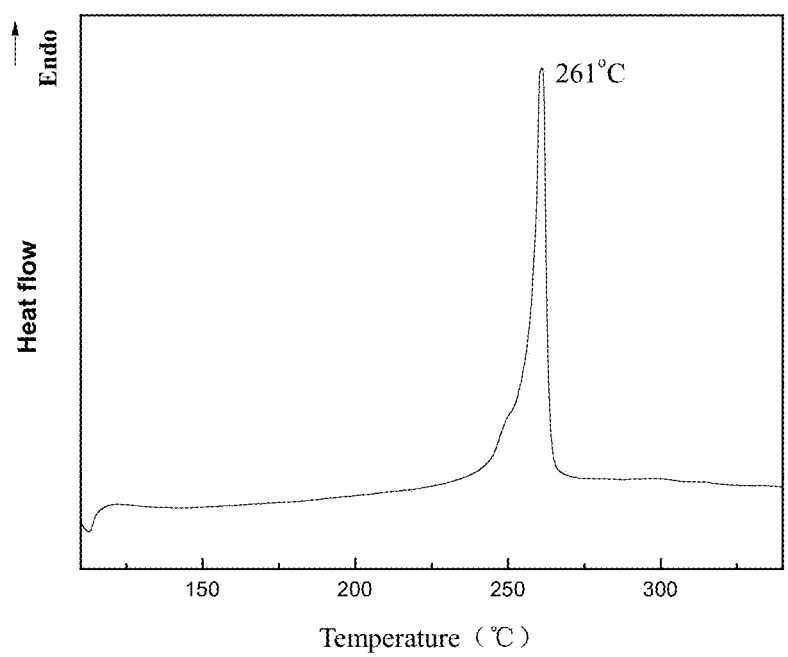
FIG. 21 is the differential scanning calorimetric (DSC) drawing of the compound 5 prepared by Example 7.

The structural test datum of this compound are shown as follows (nuclear magnetic hydrogen spectrogram, nuclear magnetic carbon spectrogram, nuclear magnetic phosphorus spectrogram, nuclear magnetic silicon spectrogram, mass spectrogram (MALDI-TOF), infrared spectrogram and DSC spectrogram of this compound are shown in FIG. 15, FIG. 16, FIG. 17, FIG. 18, FIG. 19, FIG. 20 and FIG. 21, respectively):

melting point: 257-261° C. (DSC peak temperature).

nuclear magnetic hydrogen spectrum (CDCl$_3$, 400 Hz, ppm): 0.87 (m, 16H), 2.28 (d, 16H), 7.37 (m, 32H), 7.42 (m, 16H), 7.61 (m, 32H).

nuclear magnetic carbon spectrum (CDCl$_3$, 400 Hz, ppm): 132.5, 131.79, 131.53, 130.7, 128.8, 22.69.

nuclear magnetic phosphorus spectrum (CDCl$_3$, 300 Hz, ppm): 32.76.

nuclear magnetic silicon spectrum (CDCl$_3$, 300 Hz, ppm): −66.72.

mass spectrum (MALDI-TOF): 2271, (M$^+$+Na$^+$).

elementary analysis (%): theoretical value, C, 59.77; H, 5.02; measured value, C, 59.46; H, 5.11.
infrared spectrum (cm$^{-1}$): 3067, 3026, 2987, 2961, 1946, 1604, 1410, 1276, 1111, 1005, 970.

It can be seen from the above, the structure of this product is correct, and is the compound represented by formula I. Its structural formula is shown as follows:

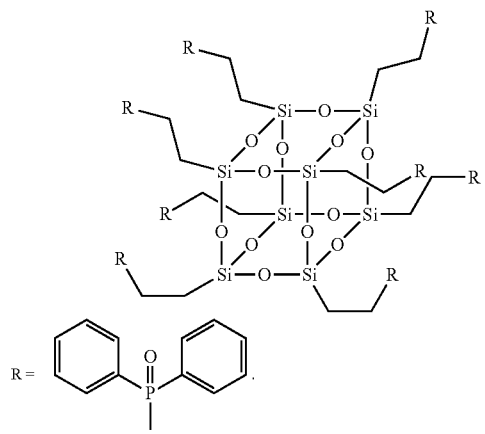

EXAMPLE 8

In a reactor equipped with nitrogen inlet, condensation tube and thermometer, 80.8 g (0.4 mol) of diphenyl phosphine oxide (DPPO) and 31.55 g (0.05 mol) of octavinyl cyclooctasilsesquioxane were sequentially added into 180 ml of 1,4-dioxane, and stirred to be clear and transparent at 27° C., 240 ml 0.2M of solution of triphenyl boron in ethyl ether was dropwise added in 6 hours at the maintained temperature of 27° C. under nitrogen protection; after the completion of dropwise addition, the reaction was kept at 27° C. for 16 hours before it was stopped, evaporating the solvent, washing with water several times, and drying, thereby obtaining 105.33 g of the white solid (compound 5), yield 94%.

The structural test datum of this compound are shown as follows (nuclear magnetic hydrogen spectrogram, nuclear magnetic carbon spectrogram, nuclear magnetic phosphorus spectrogram, nuclear magnetic silicon spectrogram, mass spectrogram (MALDI-TOF), infrared spectrogram and DSC spectrogram of this compound are shown as in Example 7, respectively):

melting point: 257-261° C. (DSC peak temperature).
nuclear magnetic hydrogen spectrum (CDCl$_3$, 400 Hz, ppm): 0.87 (m, 16H), 2.28 (d, 16H), 7.37 (m, 32H), 7.42 (m, 16H), 7.61 (m, 32H).
nuclear magnetic carbon spectrum (CDCl$_3$, 400 Hz, ppm): 132.5, 131.79, 131.53, 130.7, 128.8, 22.69.
nuclear magnetic phosphorus spectrum (CDCl$_3$, 300 Hz, ppm): 32.76.
nuclear magnetic silicon spectrum (CDCl$_3$, 300 Hz, ppm): −66.72.
mass spectrum (MALDI-TOF): 2271, (M$^+$+Na$^+$).
elementary analysis (%): theoretical value, C, 59.77; H, 5.02; measured value, C, 59.46; H, 5.11.
infrared spectrum (cm$^{-1}$): 3067, 3026, 2987, 2961, 1946, 1604, 1410, 1276, 1111, 1005, 970.

Its structural formula is shown as in Example 7.

EXAMPLE 9

In a reactor equipped with nitrogen inlet, condensation tube and thermometer, 9.20 g (0.04 mol) of 4,4'-dimethyl-diphenylphosphine oxide and 3.45 g (0.01 mol) tetramethyl-tetravinyl-cyclotetrasiloxane were sequentially added into 30 ml of toluene, and stirred to be clear and transparent at 25° C., then 18 ml 1M of solution of triethyl boron in tetrahydrofuran was dropwise added in 6 hours at the maintained temperature of 25° C. under nitrogen protection; after the completion of dropwise addition, the reaction was kept at 25° C. for 6 hours before it was stopped, evaporating the solvent, washing with water several times, and drying, thereby obtaining 10.49 g of the white solid (compound 6), yield 83%.

The structural test datum of this compound are shown as follows:

glass transition temperature (T$_g$, DSC): 60° C.
mass spectrum (MALDI-TOF): 1287, (M$^+$+Na$^+$).
elementary analysis (%): theoretical value, C, 65.53; H, 6.69; measured value, C, 65.36; H, 6.71.
infrared spectrum (cm$^{-1}$): 3414, 3056, 2969, 2930, 1633, 1594, 1481, 1435, 1407, 1261, 1180, 1162, 1121, 1072, 919.

It can be seen from the above, the structure of this product is correct, and is the compound represented by formula I. Its structural formula are shown as follows:

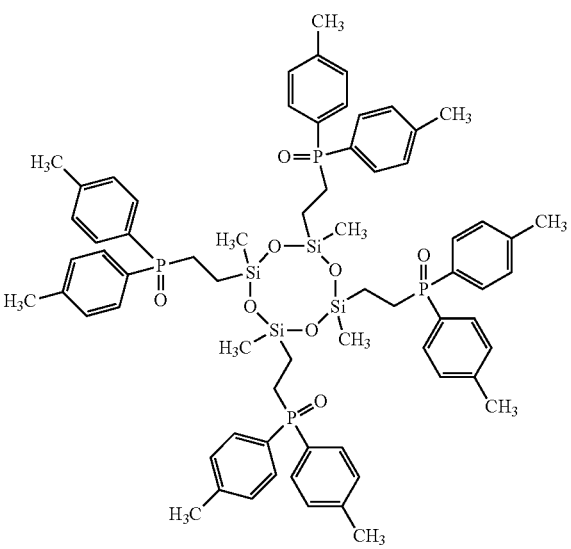

EXAMPLE 10

20 g of compound 1 prepared by Examples 1 or 2, 28 g of linear Phenol novolac (TD-2131, softening point 70° C., hydroxyl equivalent 105 g/mol, Dainippon Ink & Chemicals Inc.), 52 g of linear Phenol novolac epoxy (195LL, softening point 65° C., epoxide equivalent 195 g/mol, Yuka Shell Epoxy KK), and 0.5 g of 2-ethyl-4-methylimidazole were heated to 120° C. to melt and blend uniformly, and cast to the mould after deaeration, cured for 3 hours at 150° C., and post-cured for 2 hours at 180° C., thereby the flame retardant epoxy resin having the excellent comprehensive properties was obtained. Its tensile strength is 88 MPa, its elongation at break is 5.9%, its bending strength is 136 MPa, and its flame retardant property reaches Grade UL94 V-0.

EXAMPLE 11

25 g of compound 5 prepared by Examples 7 or 8, 32 g of linear Phenol novolac (TD-2131, softening point 70° C., hydroxyl equivalent 105 g/mol, Dainippon Ink & Chemicals Inc.), 61 g of linear Phenol novolac epoxy (195LL, softening point 65° C., epoxide equivalent 195 g/mol, Yuka Shell Epoxy KK), and 0.7 g of triphenyl phosphine were heated to 120° C. to melt and blend uniformly, and cast to the mould after deaeration, cured for 3 hours at 150° C., and post-cured for 2 hours at 180° C., thereby the flame retardant epoxy resin having the excellent comprehensive properties was obtained. Its flame retardant property reaches Grade UL94 V-0.

EXAMPLE 12

30 g of compound 3 prepared by Example 4, 50 g of linear Phenol novolac (TD-2131, softening point 70° C., hydroxyl equivalent 105 g/mol, Dainippon Ink & Chemicals Inc.), and 15 g of hexamethylene tetramine were heated to blend uniformly, and the materials which have the flame retardant level of Grade UL94 V-0 were obtained after the complete cure.

EXAMPLE 13

90 g of compound 4 prepared by Examples 5 or 6, and 270 g of polycarbonate (PC) were heated and melted, then blended uniformly, and injection-molded to process into test strip, which was tested after rubbed down. The flame retardant level of this material is Grade UL94 V-0.

EXAMPLE 14

30 g of compound 5 prepared by Examples 7 or 8, and 90 g of polyethylene glycol terephthalate (PET) were heated and melted, then blended uniformly, and injection-molded to process into test strip, which was tested after rubbed down. The flame retardant level of this material is Grade UL94 V-0.

EXAMPLE 15

30 g of compound 6 prepared by Example 9, and 95 g of polysulfone ($M_n$: 16000 g/mol, Aldrich) were heated and melted, then blended uniformly, and injection-molded to process into test strip, which was tested after rubbed down. The flame retardant level of this material is Grade UL94 V-0.

EXAMPLE 16

30 g of compound 1 prepared by Examples 1 or 2, and 90 g of polyphenyl ether ($M_n$: 20000 g/mol, Aldrich) were heated and melted, then blended uniformly, and injection-molded to process into test strip, which was tested after rubbed down. The flame retardant level of this material is Grade UL94 V-0.

EXAMPLE 17

30 g of compound 2 prepared by Example 3, and 95 g of polyamide (nylon 66, Aldrich) were heated and melted, then blended uniformly, and injection-molded to process into test strip, which was tested after rubbed down. The flame retardant level of this material is Grade UL94 V-0.

EXAMPLE 18

30 g of compound 3 prepared by Example 4, and 85 g of polystyrene were heated and melted, then blended uniformly, and injection-molded to process into test strip, which was tested after rubbed down. The flame retardant level of this material is Grade UL94 V-0.

EXAMPLE 19

30 g of compound 2 prepared by Example 3, and 90 g of polyvinyl chloride were heated and melted, then blended uniformly, and injection-molded to process into test strip, which was tested after rubbed down. The flame retardant level of this material is Grade UL94 V-0.

EXAMPLE 20

30 g of compound 5 prepared by Examples 7 or 8, and 85 g polymethyl methacrylate (PMMA) were heated and melted, then blended uniformly, and injection-molded to process into test strip, which was tested after rubbed down. The flame retardant level of this material is Grade UL94 V-0.

EXAMPLE 21

30 g of compound 1 prepared by Examples 1 or 2, 90 g of polyphenyl thioether were heated and melted, then blended uniformly, and injection-molded to process into test strip, which was tested after rubbed down. The flame retardant level of this material is Grade UL94 V-0.

EXAMPLE 22

30 g of compound 1 prepared by Examples 1 or 2, and 95 g of PC/ABS alloy were heated and melted, then blended uniformly, and injection-molded to process into test strip, which was tested after rubbed down. The flame retardant level of this material is Grade UL94 V-0.

EXAMPLE 23

20 g of compound 1 prepared by Examples 1 or 2, and 20 g of polyether polyol N220 (number average molecular weight $M_n$=2000 g/mol) were heated and stirred to blend uniformly, then mixed uniformly with 50 g of toluene-diisocyanate, and injection-molded to process into test strip, which was tested after rubbed down. The flame retardant level of this material is Grade UL94 V-0.

COMPARATIVE EXAMPLE 1

28 g of linear Phenol novolac (TD-2131, softening point 70° C., hydroxyl equivalent 105 g/mol, Dainippon Ink & Chemicals Inc.), 52 g of linear Phenol novolac epoxy (195LL, softening point 65° C., epoxide equivalent 195 g/mol, Yuka Shell Epoxy KK), and 0.5 g of triphenyl phosphine were heated to 120° C. to melt and blend uniformly, and cast to the mould after deaeration, cured for 3 hours at 150° C., and post-cured for 2 hours at 180° C., thereby the flame retardant epoxy resin having the excellent comprehensive properties was obtained. Its tensile strength is 67 MPa, its elongation at break is 3.4%, its bending strength is 110 MPa, and its flame retardant property reaches Grade UL94 not V-2.

Comparing Examples 10-23 with Comparative Example 1, the results indicate that it can make high molecular materials having very good flame retardant properties after the compounds containing phosphorus and silicon represented by formula I provided by the present invention are added into the high molecular materials in a certain proportion.

Industrial Application

A new type of compound containing phosphorus and silicon is prepared by the present invention using the cheap organic boron catalyst, and employing the addition reaction of diphenyl phosphine oxide and derivatives thereof with silicone containing carbon-carbon double bonds. Such compounds have the properties of hydrolytic resistance, easy purification, and low synthesis cost, etc. Phosphorus and silicon elements in the molecular structures of such compounds both can act as the flame retardants solely, and meantime can work synergistically, thereby enduing the common polymeric materials with the excellent flame retardant property.

The invention claimed is:

1. Compounds having formula I,

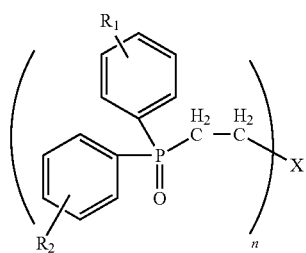

formula I where, in formula I, $R_1$ and $R_2$ are both selected from the group consisting of any one of H and alkyl that has total carbon atoms of 1-4; n is an integer of 1-20; and X is

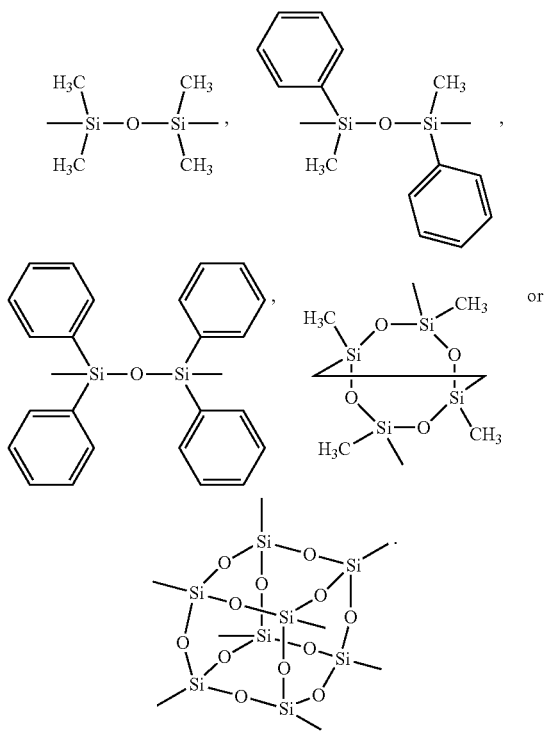

2. A method for preparing the compound having formula I of claim 1, comprising the following steps: after dissolving the compounds having formula II and vinylsiloxanes having formula III in solvent a, adding an organic boron solution into this system for reaction, and then obtaining the compounds having formula I after the completion of the reaction;

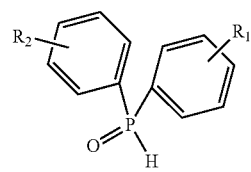

formula II

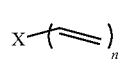

formula III

In the formula II and formula III, the definitions to $R_1$, $R_2$, n and X are all the same as claim 1.

3. The method according to claim 2, wherein the solvent a is selected from the group consisting of at least one of alcohol compounds, saturated hydrocarbon compounds, aromatic compounds, nitrile compounds, ketone compounds, tetrahydrofuran, 1,4-dioxane, N,N-dimethylformamide, N,N-dimethylacetamide, dimethylsulfoxide and N-methylpyrrolidone; wherein the alcohol compounds are selected from the group consisting of at least one of methanol, ethanol, propanol, pentanol, n-butanol, isopropanol, isobutanol, isopentanol, glycol and ethylene glycol monomethyl ether, particularly at least one of methanol, ethanol, propanol and isopropanol; wherein the saturated hydrocarbon compounds are selected from the group consisting of at least one of pentane, hexane, heptane, octane, nonane, decane, cyclopentane, cyclohexane and cycloheptane, particularly at least one of pentane, hexane, heptane, cyclopentane and cyclohexane; the aromatic compounds are selected from the group consisting of at least one of benzene, toluene and xylene, particularly at least one of toluene and xylene; the nitrile compounds are selected from the group consisting of at least one of acetonitrile and propionitrile, particularly acetonitrile; the ketone compounds are selected from the group consisting of at least one of acetone, butanone, 2-butanone and 2-pentanone, particularly at least one of acetone, butanone and 2-butanone;

the organic borons are selected from the group consisting of at least one of trimethyl boron, triethyl boron, tripropyl boron, triisopropyl boron, tributyl boron and triphenyl boron; in the organic boron solution, the solvent is selected from the group consisting of at least one of ethyl ether, tetrahydrofuran and n-hexane.

4. The method according to claim 3, wherein a feeding molar ratio of the compounds having formula II and vinylsiloxanes having formula III is n:1, wherein, n is an integer of 1-20, particularly an integer of 2-8; and a usage ratio of the solvent a and the compounds having formula II is 100~2000 ml:1 mol, particularly 500~1500 ml:1 mol.

5. The method according to claim 3, wherein in the dissolving step, a temperature is 0~50° C., particularly 10~45° C.

6. The method according to claim 3, wherein a concentration of the organic boron solution is 0.1 M~10M, particularly 0.5~5M; a feeding molar ratio of the organic boron and the compounds having formula II is 0.01~10:1, particularly 0.1~5:1.

7. The method according to claim 3, wherein
in the reacting step, a temperature is 0~50° C., particularly 10~45° C., a time is 0.5~40 hours, particularly 1~35 hours; wherein
the reacting step is performed in inert atmosphere; the inert atmosphere is selected from the group consisting of at least one of nitrogen atmosphere and argon atmosphere, particularly nitrogen atmosphere.

8. A flame retardant material comprising the compounds having formula I of claim 1.

9. A method of use of the compounds comprising use of the compounds having formula I of claim 1 for preparing flame retardant materials.

10. The flame retardant materials or use thereof according to claim 9, wherein the flame retardant materials are selected from the group consisting of at least one of flame retardant thermoplastic engineering plastic, flame retardant thermosetting resin composition, flame retardant encapsulating materials, flame retardant adhesive, flame retardant laminated ply and flame retardant fiber reinforced materials, the flame retardant encapsulating materials particularly are flame retardant integrated circuit encapsulating materials.

* * * * *